United States Patent
Furukawa et al.

(10) Patent No.: US 8,067,537 B2
(45) Date of Patent: Nov. 29, 2011

(54) COMPOSITION AND METHOD FOR TREATMENT OF STOMATITIS

(75) Inventors: Satoru Furukawa, Tokyo (JP); Kenjiro Shimada, Ibaraki (JP); Dean Jones, Atlanta, GA (US); Thomas Ziegler, Lilburn, GA (US)

(73) Assignees: Kyowa Hakko Bio Co., Ltd., Tokyo (JP); Emory University, Atlanta, GA (US)

( * ) Notice: Subject to any disclaimer, the term of this patent is extended or adjusted under 35 U.S.C. 154(b) by 811 days.

(21) Appl. No.: 11/574,682

(22) PCT Filed: Sep. 2, 2005

(86) PCT No.: PCT/US2005/031364
§ 371 (c)(1),
(2), (4) Date: Mar. 5, 2007

(87) PCT Pub. No.: WO2006/028991
PCT Pub. Date: Mar. 16, 2006

(65) Prior Publication Data
US 2007/0259024 A1 Nov. 8, 2007

Related U.S. Application Data

(60) Provisional application No. 60/607,053, filed on Sep. 3, 2004.

(51) Int. Cl.
*A61K 38/06* (2006.01)
(52) U.S. Cl. .......... 530/331; 514/247; 514/21.9
(58) Field of Classification Search .......... 530/331; 514/247, 21.9
See application file for complete search history.

(56) References Cited

U.S. PATENT DOCUMENTS

| | | | |
|---|---|---|---|
| 2,250,553 A | 7/1941 | Ruskin et al. | |
| 4,405,610 A * | 9/1983 | Krnjevic | 514/45 |
| 4,508,898 A * | 4/1985 | Ogilvie | 544/211 |
| 4,975,434 A * | 12/1990 | Marquez et al. | 514/274 |
| 5,204,114 A | 4/1993 | Demopoulos et al. | |
| 6,159,500 A | 12/2000 | Demopoulos et al. | |
| 6,514,955 B1 * | 2/2003 | Van Dyke | 514/171 |
| 2002/0136763 A1 * | 9/2002 | Demopoulos et al. | 424/451 |

FOREIGN PATENT DOCUMENTS

| | | |
|---|---|---|
| EP | 0834301 | 4/1998 |
| EP | 1402892 | 3/2004 |
| EP | 1655292 | 5/2006 |

OTHER PUBLICATIONS

MacPhail (Seminars in Cutaneous Medicine and Surgery 16(4), 301-307, 1997).*
Casiglia (General Dentistry 50(2), 157-166, 2002).*
Kyama (Kanazawa Irigaku Sosho, XP002463743, vol. 83, pp. 23-36, 1969).*
English translation of: Kyama (Kanazawa Irigaku Sosho, XP002463743, vol. 83, pp. 23-36, 1969).*
International Search Report for PCT/US05/31364 mailed Feb. 24, 2006.
Osaki, et al. Prophylaxis of Oral Mucositis Asssociated with Chemoradiotherapy for Oral Carcinoma by Azelastine Hydrochloride (Azelastine) with other Antioxidants, Head and Neck, vol. 16, No. 4, pp. 331-339, 1994. XP009088468.

* cited by examiner

*Primary Examiner* — David Lukton
(74) *Attorney, Agent, or Firm* — Leydig, Voit & Mayer, Ltd.

(57) ABSTRACT

A composition and a method effective in preventing or treating stomatitis are presented. The composition contains glutathione or a pharmaceutically acceptable salt thereof and/or orotic acid or a derivative thereof or a pharmaceutically acceptable salt thereof is provided.

12 Claims, No Drawings

COMPOSITION AND METHOD FOR TREATMENT OF STOMATITIS

CROSS-REFERENCE TO PRIOR APPLICATION

This is a U.S. National Phase Application under 35 U.S.C. §371 of International Patent Application No. PCT/US2005/031364 filed Sep. 2, 2005, and claims the benefit of U.S. Provisional Application No. 60/607,053, filed Sep. 3, 2004, both of which are incorporated by reference herein. The International Application was published in English on Mar. 16, 2006 as WO 2006/028991 A1 under PCT Article 21(2).

TECHNICAL FIELD

The present invention relates to a composition and a method for use in prevention or treatment of stomatitis.

BACKGROUND ART

Stomatitis is a general term for an inflammatory disease occurring in the oral cavity mucous membrane such as the tongue, gums, lips, inside of the cheeks, and the like.

Stomatitis is thought to be caused by viruses or bacteria present within the mouth infecting the mucous membrane inside the oral cavity in areas where there has been damage by injuries from biting with teeth, hot foods, drying out of the mucous membrane, and the like. In addition, with stomatitis that occurs as a side-effect of radiation therapy or chemotherapy, the mucous membrane cells are damaged by the effect of active oxygen, and mucositis occurs. Furthermore, defense mechanisms inside the oral cavity are disrupted, and secondary infection by viruses and bacteria in the mouth occur.

Stomatitis caused by radiation therapy or chemotherapy is particularly serious, and when a complication such as sepsis occurs, mortality reaches 40-60% (The Lancet, 351, 1501-1505 (1998)). In addition, unlike stomatitis due to other causes, the patients can not take meals because of the pain, and from the standpoint of quality of life (QOL) and medical costs, this is an extremely important problem.

For the treatment of stomatitis, creams and patches of steroid medicine are known, but their effectiveness greatly varies between individuals. In health food related products, vitamins centering around the Vitamin B group, zinc, propolis, *Lactobacillus bifidus*, green juice, and the like are said to be somewhat effective for the treatment of stomatitis, but these do not always produce satisfactory results.

With regard to treatment of serious stomatitis caused by radiation therapy and chemotherapy, GM-CSF [European Journal of Cancer, 37 (16), 1971-1975 (2001)] and zinc-carnosine hydrochloride [Nippon acta radiologica 62 (4), 144-150 (2002)], and the like have been considered, but there are still no approved treatment medicines.

DISCLOSURE OF INVENTION

The object of the present invention is to provide a composition and a method that is effective in the prevention or treatment of stomatitis.

The present invention relates to the following (1)-(20).
(1) A composition for prevention or treatment of stomatitis, comprising:
glutathione or a pharmaceutically acceptable salt thereof; and/or orotic acid or a derivative thereof or a pharmaceutically acceptable salt thereof.
(2) The composition according to (1), wherein said glutathione is a reduced glutathione or oxidized glutathione.
(3) The composition according to (1), wherein said orotic acid or a derivative thereof or a pharmaceutically acceptable salt thereof is free orotic acid or zinc orotate.
(4) The composition according to in (1), wherein stomatitis is a result of radiation therapy or chemotherapy.
(5) The composition according to (1), wherein said composition is a medicine, food or drink, or food or drink additive.
(6) The composition according to (1), wherein said composition is a chewable tablet, sublingual tablet, chewing gum, gummy candy, or drop.
(7) A method for prevention or treatment of stomatitis, comprising:
administering a composition comprising glutathione or a pharmaceutically acceptable salt thereof, and/or orotic acid or a derivative thereof or a pharmaceutically acceptable salt thereof.
(8) The method according to (7), wherein said glutathione is a reduced glutathione or oxidized glutathione.
(9) The method according to (7), wherein said orotic acid or a derivative thereof or a pharmaceutically acceptable salt thereof is free orotic acid or zinc orotate.
(10) The method according to (7), wherein stomatitis is a result of radiation therapy or chemotherapy.
(11) The method according to (7), wherein said composition is administered as a medicine, food or drink, or food or drink additive.
(12) The method according to (7), wherein said composition is administered as a chewable tablet, sublingual tablet, chewing gum, gummy candy, or drop.
(13) A method comprising:
administering a composition comprising glutathione or a pharmaceutically acceptable salt thereof, and/or orotic acid or a derivative thereof or a pharmaceutically acceptable salt thereof to prevent or treat stomatitis.
(14) The method according to (13), wherein said glutathione is a reduced glutathione having a structure of gamma-L-Glu-L-Cys-Gly.
(15) The method according to (13), wherein said glutathione is an oxidized glutathione, which is a glutathione dipeptide in which two molecules of reduced glutathione are bonded by a SS bond.
(16) The method according to (13), wherein said orotic acid or a derivative thereof or a pharmaceutically acceptable salt thereof is free orotic acid or zinc orotate.
(17) The method according to (13), wherein stomatitis is a result of radiation therapy or chemotherapy.
(18) The method according to (13), wherein said composition is administered as a medicine, food or drink, or food or drink additive.
(19) The method according to (13), wherein said composition is administered as a chewable tablet, sublingual tablet, chewing gum, gummy candy, or drop.
(20) Use of a composition comprising glutathione or a pharmaceutically acceptable salt thereof, and/or orotic acid or a derivative thereof or a pharmaceutically acceptable salt thereof for producing a medicine, food or drink, or food or drink additive.

In an implementation of the present invention, glutathione includes reduced glutathione and oxidized glutathione.

Reduced glutathione is a tripeptide having a structure of gamma-L-Glu-L-Cys-Gly. Oxidized glutathione is a glutathione dipeptide in which two molecules of reduced glutathione are bonded by a SS bond.

The reduced glutathione and oxidized glutathione used in an embodiment of the present invention can be obtained by any method. For example, methods for producing reduced glutathione include an extraction method from microorganisms such as yeast and the like (Methods in Enzymology, 3, 603 (1957)), a chemical synthesis method [Bull. Chem. Soc. Jpn. 53, 2529 (1980)], an enzyme method (Japanese Published Unexamined Application No. 74595/1986), and the like. For producing oxidized glutathione, there is a method described in [Acta Biochem. Pol., 17, 175 (1970)].

As methods for producing reduced glutathione, a chemical synthesis method and an extraction method from yeast are exemplified.

1. Chemical Synthesis Method of Reduced Glutathione

Reduced glutathione is chemically synthesized by a method described in [Bull. Chem. Soc. Jpn. 53 2592 (1980)].

N-formyl-L-2-amino-4-cyanobutyrate ethyl ester is condensed with ethyl L-cysteinyl glycinate to obtain (4R)-2-[(3S)-3-ethoxycarbonyl-3-(formyl amino) propyl]-4-(ethoxycarbonyl methyl carbamoyl)-2-thiazoline. Next, after saponification in acetone aqueous solution at approximately −15 degrees C., it is treated with dilute sulfuric acid (pH 4), to obtain formyl glutathione. Next, by hydrolyzing with 0.5 mmol/l of sulfuric acid, the formyl group is removed, and free glutathione is obtained. This is further purified as needed. In this further purification, pure glutathione is obtained by converting free glutathione into its copper thiolate and treating with hydrogen sulfide.

2. Method for Extracting Reduced Glutathione from Yeast

Reduced glutathione is extracted from yeast by the method described in [Methods in Enzymology, 3, 603 (1957)].

An equal weight of 10% trichloroacetate (TCA) is added to a yeast extract. The residue obtained by centrifugation is further extracted twice with half the initial volume of TCA. The extracts are combined, and cadmium chloride solution at a quarter of the volume of the extraction product is added. Sodium hydroxide (10 mol/l) is added to make the solution to have a pH of 5. Afterwards, the pH is adjusted to 6.5 by using bicarbonate. The precipitated cadmium complex is kept for 1 hour at 0 degrees C., and is then washed twice with ice-chilled distilled water. The precipitate is dissolved in the minimum amount of 2 mol/l sulfuric acid. For every 10 mg of predicted yield of glutathione, 3 mL of 0.5 mol/l sulfuric acid is added. The solution is filtered as needed, and the amount of glutathione is determined in aliquot units. The solution is heated to 40 degrees C., and for every 10 mg of glutathione, a copper oxide suspension solution containing 2.5 mg of copper oxide is added dropwise while gently shaking. The resulting precipitate is left for several hours at 0 degrees C., then centrifuged, washed twice with 0.5 mol/l of sulfuric acid, washed three times with distilled water, and washed twice with methanol. In order to isolate the free glutathione, the glutathione copper complex is decomposed by hydrogen in an aqueous suspension solution. After removing the copper sulfite, the solution is dried by freeze drying.

The composition of the present invention may be a composition which comprises either reduced glutathione or oxidized glutathione singly, or may be a composition which simultaneously comprises reduced glutathione and oxidized glutathione.

In addition, the reduced glutathione and oxidized glutathione comprised in the composition of an implementation of the present invention may exist in the composition as a pharmaceutically acceptable salt of reduced glutathione and oxidized glutathione. Examples of pharmaceutically acceptable salts (in the form of water-soluble, oil-soluble, or dispersible products) of reduced glutathione and oxidized glutathione include standard non-toxic salts formed from inorganic acids, organic acids, or bases, or quaternary ammonium salts, and the like.

Salts formed from inorganic acids or organic acids include, for example, acetate, adipate, alginate, aspartate, benzoate, benzenesulfonate, bisulfate, butyrate, citrate, camphorate, camphosulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, undecanoate, and the like.

Examples of salts formed from bases include ammonium salts, alkali metal salts such as sodium salt and potassium salt, alkaline earth metal salts such as calcium salt and magnesium salt, salts with organic bases such as dicyclohexylaminate salts and N-methyl-D-glucamine, and salts with amino acids such as arginine and lysine.

In addition, examples of the quaternary ammonium salts include lower alkyl halides, such as methyl, ethyl, propyl and butyl chlorides, bromides and iodides; dialkyl sulfates such as dimethyl sulfate, diethyl sulfate and dibutyl sulfate, diamyl sulfate; long chain halides such as decyl, lauryl, myristyl and stearyl chlorides, bromides and iodides; and salts quaternized by such agents as aralkyl halides such as benzyl bromide and phenethyl bromide. Other pharmaceutically acceptable salts include the sulfate salt ethanolate, sulfate salts and the like.

In addition, in an implementation of the present invention, substances that are metabolized into reduced glutathione in the body, for example, N-acetyl cysteine and the like can be used instead of glutathione.

In an implementation of the present invention, orotic acid represents an uracil-4-carboxylic acid. The orotic acid, or a derivative thereof, or a pharmaceutically acceptable salt thereof used may be derived from microbes, obtained through chemical synthesis, or a commercial product.

Orotic acid derived from microbes include, for example, the orotic acid obtained by the method described in U.S. Pat. No. 5,013,656.

Derivatives of orotic acid include 4-ester substitutions in which alkyl groups with 1-6 carbon(s) such as methyl, ethyl, butyl, propyl, pentyl and hexyl form an ester bond to the 4-position carboxylic acid, and derivatives in which more than one hydrogen(s) in the 1, 2, 3, 6 position is substituted with an alkyl group having 1-6 carbon(s) such as methyl, ethyl, butyl, propyl, pentyl and hexyl or with an alkoxy group having an alkyl group with 1-6 carbon(s) such as methyl, ethyl, butyl, propyl, pentyl and hexyl.

Pharmaceutically acceptable salts of orotic acid or derivatives thereof include alkali metal salts such as sodium salt and potassium salt; alkaline earth metal salts such as magnesium salt and calcium salt; heavy metal salts such as zinc salt; ammonium salts such as ammonium and tetramethyl ammonium; and organic amine addition salts such as morpholine and piperidine.

In an implementation of the present invention, stomatitis include those caused by mechanical damage, poor oral hygiene, lowered overall health status, cancer treatment, and the like.

Mechanical damage occurs when dentures do not fit properly, when poor teeth alignment results in teeth hitting the mucous membrane, when there are burns due to eating hot foods, when there is drying out of the mucous membrane inside the oral cavity, and the like.

Poor oral hygiene can occur when saliva secretion is inadequate because water and food intake is inadequate; when cleaning of the mouth such as brushing of teeth and rinsing of the mouth is not possible.

Lowered overall health status can occur when there is weakening due to illness or strain, when nutritional status is poor from anemia or vitamin deficiency of vitamin B2 and the like, when antibiotics and steroids are used in large doses, when there are diseases such as leukemia or aplastic anemia, and the like.

Cancer treatment includes radiation therapy, chemotherapy, and the like.

The composition of an implementation of the present invention can be used as medicine, food or drink, or food or drink additive.

When the composition is used as a medicine, it is preferably used as an oral medicine, formulation for mouthwash or gargle, and oral cavity ointment.

In an oral medicine, glutathione or a pharmaceutically acceptable salt thereof and/or orotic acid or a derivative thereof or a pharmaceutically acceptable salt thereof are mixed with a carrier as needed, and the oral medicine is produced according to techniques well-known in the art of pharmaceutical formulation.

When producing an oral medicine, additives such as excipients, binders, disintegrators, lubricants, dispersing agents, suspending agents, emulsifiers, diluents, buffering agents, anti-oxidants, anti-bacterial agents, and the like can be used.

Examples of the form of oral medicine include tablets, such as chewable tablets, sublingual tablets, slow-release tablets, powders, granules, emulsions, syrups, capsules. However, because of their long retention time within the mouth, chewable tablets and sublingual tablets are preferred.

For example, when the form of oral medicine is a tablet, powder, granule, or the like, these are formulated by adding excipients, disintegrators, lubricants, binders, surfactants, and plasticizers. Examples of excipients include sugars such as lactose, white sugar, glucose, sucrose, mannitol and sorbitol; starches of potato, wheat, corn, and the like; inorganic substances such as calcium carbonate, calcium sulfate, sodium bicarbonate and sodium chloride; and plant powders such as licorice powder and gentian powder. Examples of disintegrators include starches, agar, gelatin powder, crystalline cellulose, carmelose sodium, carmelose calcium, calcium carbonate, sodium bicarbonate, sodium alginate, and the like. Examples of lubricants include magnesium stearate, talc, hydrogenated vegetable oil, macrogol, silicon oils, and the like. Examples of binders include polyvinyl alcohol, hydroxypropyl cellulose, methyl cellulose, ethyl cellulose, carmelose, gelatin, starch solution, and the like. Examples of surfactants include fatty acid esters, and the like. Examples of plasticizers include glycerine and the like.

When the form of oral medicine is a liquid preparation such as an emulsion or syrup, this is formulated by adding water; sugars such as sucrose, sorbitol and fructose; glycols such as polyethylene glycol and propylene glycol; oils such as sesame oil, olive oil and soybean oil; antiseptics such as p-hydroxybenzoic acid esters; and flavoring agents such as strawberry flavor and peppermint. In the liquid preparation described above, glutathione or a pharmaceutically acceptable salt thereof, orotic acid or a derivative thereof or a pharmaceutically acceptable salt thereof can each be of any concentration. Preferably, the concentration is 10-200 mmol/l, more preferably 10-50 mmol/l. In addition, the pH of the liquid preparation can be of any pH as long as the glutathione or a pharmaceutically acceptable salt thereof, orotic acid or a derivative thereof or a pharmaceutically acceptable salt thereof is stable. Preferably, the pH is in the range of 4.0-6.0.

When the form of oral medicine is a capsule, it is charged into a hard capsule. Alternatively, the medicine is packaged and molded in a capsule base material and formulated as a soft capsule. An example of a capsule base material is gelatin. In order to have plasticity in the soft capsule, glycerine or sorbitol is added. In addition, dyes, titanium oxide as a light blocking agent, barium sulfate, precipitated calcium carbonate, paraoxybenzoic acid ester as an antiseptic and the like can be added.

Mouthwashes or gargle formulations are formulated by adding antibacterials, surfactants, co-surfactants, oil, water and other additives, and sweeteners/flavor and odor enhancers that are well-known in the art of pharmaceutical formulation to glutathione or a pharmaceutically acceptable salt thereof and/or orotic acid or a derivative thereof or a pharmaceutically acceptable salt thereof.

Glutathione or a pharmaceutically acceptable salt thereof, orotic acid or a derivative thereof or a pharmaceutically acceptable salt thereof contained in the mouthwash or gargle formulation can each be of any concentration. Preferably, the concentration is 10-200 mmol/l, and more preferably 10-50 mmol/l. In addition, the pH of the liquid preparation can be of any pH as long as the glutathione or a pharmaceutically acceptable salt thereof, orotic acid or a derivative thereof or a pharmaceutically acceptable salt thereof is stable. Preferably, the pH is in the range of 4.0-6.0.

Oral cavity ointments are formulated by having glutathione or a pharmaceutically acceptable salt thereof and/or orotic acid or a derivative thereof or a pharmaceutically acceptable salt thereof combined with selected additives. Examples of additives include distilled water for injection, purified water, calcium carboxymethylcellulose, sodium carboxymethylcellulose, lactose, sorbitol, mannitol, white sugar, cornstarch, crystalline cellulose, lactitol, cellulose derivative, gum arabic, gum tragacanth, gelatin, polysorbate 80, talc, magnesium stearate, water, ethanol, white vaseline, glycerine, fat, fatty oil, glycols, higher alcohols such as stearyl alcohol, plastibase, paraffin, beeswax, polyoxyethylene hardened castor oil, saccharin, pineapple syrup, and the like.

When glutathione or a pharmaceutically acceptable salt thereof, orotic acid or a derivative thereof or a pharmaceutically acceptable salt thereof are used in combination for the medicine, the medicine can be used or administered as a single preparation (mixture) or a combination of preparations as long as it is formulated to contain each of these components. When a combination of preparations is used, it can be administered simultaneously or separately at different times.

When administering a combination of preparations, as an example, the following are each formulated separately as described previously: (a) glutathione or a pharmaceutically acceptable salt thereof and (b) orotic acid or a derivative thereof or a pharmaceutically acceptable salt thereof. These are created as kits. Using this kit, each component may be administered simultaneously or at different times by the same route or by different routes of administration to the same subject.

The kit comprises at least two or more containers (vial, bag, and the like, for example) and the contents. The material and shape and the like of the containers are not limited as long as there is no denaturation of the components of the contents from external temperature and light during storage and there is no elution of the chemical components from the containers or the like. The kit which can administer the first component and the second component, which are the contents, by the same route or by differing routes are used.

When the composition is administered to humans as medicine, the dose and administration frequency will depend on the form of administration, age, weight, symptoms, and the like. However, in general, for glutathione or a pharmaceutically acceptable salt thereof, orotic acid or a derivative thereof or a pharmaceutically acceptable salt thereof, the dose is 1-10000 mg, preferably 10-2000 mg and more preferably 50-500 mg once a day to several times a day. The administration period is not limited, however, it is normally 1 day to 1 year, and preferably 1 week to 3 months.

The food or drink additive is prepared by the same method as the oral medicine described above. This food or drink additive is generally mixed or dissolved with other food or drink additives as needed. For example, they are produced as powders, granules, pellets, tablets, and various liquid agents.

The food or drink is a food or drink in which glutathione or a pharmaceutically acceptable salt thereof and/or orotic acid or a derivative thereof or a pharmaceutically acceptable salt thereof is added.

The food or drink other than those produced by adding glutathione or a pharmaceutically acceptable salt thereof and/or orotic acid or a derivative thereof or a pharmaceutically acceptable salt thereof may be produced by using general methods for producing food and drink.

The food or drink is produced using a granulation method such as fluid bed granulation, agitation granulation, extrusion granulation, rolling granulation, air stream granulation, compression molding granulation, cracking granulation, atomizing granulation and prilling; coating method such as pan coating, fluid bed coating and dry coating; expansion methods such as puff dry, excess steam method, foam mat method and microwave heating method; and extrusion methods using extrusion granulators, extruders, and the like.

The food or drink can be juices; soft drinks; teas; fermented lactic drink; fermented milk; cold desserts; butter; cheese; yogurt; dairy products such as processed milk and skim milk; meat products such as ham, sausage and hamburger; fish paste products such as steamed fish paste, fish sausage and fried fish ball; egg products such as omelets and egg tofu; sweets such as cookies, jellies, chewing gums, candies, gummy candies, drops, throat drops, and snacks; breads; noodles; pickles; smoked foods; dried foods; soy sauce preserved foods; salted foods; soups; seasonings; and the like. Chewing gum, candy, gummy candy, drop, throat drop, and the like are preferred due to their long retention time in the mouth.

In addition, the food or drink can be a powder food, sheet food, jarred food, canned food, retort food, capsule food, tablet food, liquid food, drink, or the like.

Food or drink additives normally used in food or drink can be added to the food or drink or the food or drink additive. Examples of food or drink additives include: sweetener, coloring agent, preservative, thickness stabilizer, antioxidant, color former, bleach, antifungal agent, gum base, bitter flavoring, enzyme, brightening agent, acidulant, seasoning, emulsifier, strengthening agents, production agent, fravoring, spice extract, and the like.

The food and drink can be used as a health food for prevention or treatment of stomatitis or as a functional food product and the like.

The amount of glutathione or a pharmaceutically acceptable salt thereof, orotic acid or a derivative thereof or a pharmaceutically acceptable salt thereof added to the food or drink or the addition amount of food additive depends on the type of food or drink and the effectiveness anticipated by the intake of the food or drink. However, in general, the glutathione or a pharmaceutically acceptable salt thereof and/or orotic acid or a derivative thereof or a pharmaceutically acceptable salt thereof is added so that the content is 0.1-90% by weight, preferably 0.3-70% by weight, and more preferably 1-50% by weight.

The intake amount of the food or drink depends on the form of intake, age and weight of the person, and the like. However, in general, for an adult, the amount of glutathione or a pharmaceutically acceptable salt thereof, orotic acid or a derivative thereof or a pharmaceutically acceptable salt thereof is 1-10000 mg per day, preferably 10-2000 mg, and more preferably 50-500 mg. This can be once a day or divided over several times in one day. There are no limitations on the intake period, but in general, it is 1 day-1 year, preferably 1 week-3 months.

The effectiveness in treatment of stomatitis by glutathione and/or orotic acid or a pharmaceutically acceptable salt thereof is shown below in the test examples.

TEST EXAMPLE 1

Effectiveness of Glutathione in Treatment of Cat Stomatitis

A cat (15 years old, weight 1.9 kg) had developed AIDS and had a serious case of, chronic stomatitis with no improvement seen despite nearly 10 years of treatment with interferon administration. After administering reduced glutathione at 30 mg/kg per day mixed in the feed for two weeks, dramatic improvements in the fauces erosion and gum inflammation were seen. Appetite was also improved.

TEST EXAMPLE 2

Effectiveness of Orotic Acid in Treatment of Dog Stomatitis

A poodle (14 years old, weight 3.0 kg) developed minor stomatitis presumably caused by hard tooth tartar and also developed gum inflammation. An equal part mixture composition of zinc orotate and free orotic acid was administered at 100 mg/kg per day by mixing in feed for two weeks. As a result, the stomatitis and gum inflammation were dramatically improved.

TEST EXAMPLE 3

Effectiveness of a Mixture Composition of Glutathione and Orotic Acid in Treatment of Cat Stomatitis Seven cats with stomatitis caused by bacteria, injury, hard tooth tartar, and the like were given in their feed 50 mg/kg per day of a composition of a mixture of reduced glutathione, zinc orotate, free orotic acid at a ratio of 1:0.5:1.

After the start of administration, the veterinarian evaluated the symptoms of the stomatitis every week. If the symptoms were improved within two weeks of the start of administration, this was judged to be "effective". If the symptoms were improved after two weeks from the start of administration, this was judged to be "somewhat effective". If no improvement was seen, this was judged to be "ineffective". If the symptoms were worsened, this was judged to be "worse".

As a result, there were 4 cases of "effective", 1 case of "somewhat effective", 2 cases of "ineffective", and 0 cases of "worse". The rate of effectiveness was 71.4% (5/7 animals).

BEST MODE FOR CARRYING OUT THE INVENTION

The examples of the present invention are described below.

EXAMPLE 1

Preparation of a Tablet Containing Reduced Glutathione

A tablet is prepared by the standard method with the recipe described below.

| | |
|---|---|
| Reduced glutathione | 50 mg |
| Lactose | 90 mg |
| Cornstarch | 30 mg |
| Synthetic aluminum silicate | 12 mg |
| Calcium carboxymethyl cellulose | 15 mg |
| Magnesium stearate | 3 mg |

EXAMPLE 2

Preparation of a Chewing Gum Containing Reduced Glutathione

Chewing gum is prepared by the standard method with the recipe described below.

| | |
|---|---|
| Reduced glutathione | 1.5 g |
| Gum base | 25 g |
| Sugar | 63 g |
| Millet syrup | 10 g |
| Flavoring | 1 g |

EXAMPLE 3

Preparation of a Gummy Candy Containing Zinc Orotate

Gummy candy is prepared by the standard method with the recipe described below.

| | |
|---|---|
| Zinc orotate | 1.5 g |
| Granulated sugar | 30 g |
| Millet syrup | 25 g |
| Gelatin | 10 g |
| Citric acid | 0.5 g |
| Tartaric acid | 0.3 g |
| Flavor | 1 g |
| Water | 31.7 g |

EXAMPLE 4

Preparation of a Drop Containing Reduced Glutathione and Zinc Orotate (1)

The drop is prepared using the candy base material and medicine mixture as described below.

| | |
|---|---|
| Candy base material: | |
| Maltitol (medium grain) | 35 kg |
| Corn syrup 43 degrees Baume | 21 kg |
| Medicine mixture: | |
| Polyethylene glycol (molecular weight 6,000) | 2.75 kg |
| Reduced glutathione | 5 kg |
| Zinc orotate | 2.5 kg |
| Citric acid | 60 kg |
| Wild cherry artificial flavor | 60 g |

The preparation of the candy base material is conducted as follows.

The maltitol is dissolved in 5.5 liters of water. Glucose-containing corn syrup is added, and this is mixed. At this point, colorings are added as needed to obtain the desired color. For the coloring, those that can adequately dissolve are used.

The above mixture is placed in a steam jacket kettle heated to 125 degrees C. From there, the mixture is placed in a storage container by a pump, and this is supplied to a continuous cooker. By passing the coil of the cooker, the syrup reaches a temperature of 125-150 degrees C. Afterwards, this is supplied by a steam vacuum ejector to a receiving kettle maintained at a vacuum of 28-29 inches for approximately 6-7 minutes. During this time, water is removed until the water content is reduced to approximately 1% or less, and a suitable melted candy base material is formed. By slowly cooling the melted candy base material, the candy base material is prepared.

Next, the reduced glutathione, zinc orotate, citric acid, and artificial flavor (powder) is added to polyethylene glycol to prepare the medicine mixture. This mixture is heated to approximately 90 degrees C. to make into a fluid. The resulting heated fluid mixture is rapidly added to the melted candy base material (in which the temperature has been lowered to approximately 100 degrees C. or to a temperature slightly below that). Next, after adequately kneading the entire mass, this is transferred to a spinning machine. By extruding into a lozenge shaped die, drops containing reduced glutathione and zinc orotate are prepared.

EXAMPLE 5

Preparation of Drops Containing Reduced Glutathione and Zinc Orotate (2)

The melted candy mass added with the medicine mixture obtained in Example 4 is poured onto a cooling table. After solidifying to a semi-solid mass on the cooling table, this is molded into the desired shape for the intake of unit intake amounts of reduced glutathione and zinc orotate. With this, drops containing reduced glutathione and zinc orotate are prepared.

INDUSTRIAL APPLICABILITY

With the present invention, a composition which is effective in the prevention or treatment of stomatitis and which contains glutathione or a pharmaceutically acceptable salt thereof and/or orotic acid or a derivative thereof or a pharmaceutically acceptable salt thereof is provided.

The invention claimed is:

1. A method for treatment of stomatitis, which method comprises administering a composition to a subject afflicted with stomatitis, wherein said composition is a chewable tablet, sublingual tablet, chewing gum, gummy candy, or drop which comprises (a) glutathione or a pharmaceutically acceptable salt of glutathione, and/or (b) free orotic acid or a pharmaceutically acceptable salt of orotic acid selected from the group consisting of sodium orotate, potassium orotate, magnesium orotate, calcium orotate, zinc orotate, ammonium orotate, tetramethyl ammonium orotate, morpholine orotate, and piperidine orotate, wherein one or more symptoms of stomatitis are improved in the subject.

2. The method according to claim 1, wherein said glutathione is a reduced glutathione or oxidized glutathione.

3. The method according to claim 1, wherein the composition comprises free orotic acid or zinc orotate.

4. The method according to claim 1, wherein stomatitis is a result of radiation therapy or chemotherapy.

5. The method according to claim 1, wherein said composition is administered as a medicine, food, or food additive.

6. The method according to claim 2, wherein said glutathione is a reduced glutathione.

7. The method according to claim 2, wherein said glutathione is an oxidized glutathione.

8. A method for treatment of stomatitis, which method comprises administering a composition to a subject afflicted with stomatitis, wherein said composition comprises free orotic acid or a pharmaceutically acceptable salt of orotic acid selected from the group consisting of sodium orotate, potassium orotate, magnesium orotate, calcium orotate, zinc orotate, ammonium orotate, tetramethyl ammonium orotate, morpholine orotate, and piperidine orotate, wherein one or more symptoms of stomatitis are improved in the subject.

9. The method of claim 8, where the composition comprises free orotic acid or zinc orotate.

10. The method according to claim 1, wherein stomatitis is a result of mechanical damage or poor oral hygiene.

11. A method for treatment of stomatitis resulting from radiation therapy, chemotherapy, mechanical damage, or poor oral hygiene, which method comprises administering a composition to a subject afflicted with stomatitis resulting from radiation therapy, chemotherapy, mechanical damage, or poor oral hygiene, wherein said composition comprises (a) glutathione or a pharmaceutically acceptable salt of glutathione, and/or (b) free orotic acid or a pharmaceutically acceptable salt of orotic acid selected from the group consisting of sodium orotate, potassium orotate, magnesium orotate, calcium orotate, zinc orotate, ammonium orotate, tetramethyl ammonium orotate, morpholine orotate, and piperidine orotate, wherein one or more symptoms of stomatitis resulting from radiation therapy, chemotherapy, mechanical damage, or poor oral hygiene are improved in the subject.

12. The method according to claim 11, wherein said composition is a chewable tablet, sublingual tablet, chewing gum, gummy candy, or drop.

* * * * *